United States Patent [19]
Rosenlund et al.

[11] Patent Number: 5,641,455
[45] Date of Patent: Jun. 24, 1997

[54] STERILIZER WITH GAS CONTROL

[75] Inventors: Thomas Theodore Rosenlund, Stillwater; David George Peters, Oakdale, both of Minn.

[73] Assignee: Minnesota Mining & Manufacturing Company, St. Paul, Minn.

[21] Appl. No.: 577,196

[22] Filed: Dec. 22, 1995

[51] Int. Cl.$^6$ .................................................. A61L 2/20
[52] U.S. Cl. .................. 422/28; 422/33; 422/34; 422/110; 422/119; 422/295
[58] Field of Search ........................ 422/3, 28, 33, 422/34, 110, 119, 292, 295

[56] References Cited

U.S. PATENT DOCUMENTS

| | | | |
|---|---|---|---|
| 3,054,270 | 9/1962 | Huston | 62/50.2 |
| 3,564,861 | 2/1971 | Andersen et al. | 62/48.1 |
| 3,571,563 | 3/1971 | Shulz | 219/491 |
| 3,598,517 | 8/1971 | Beecher | 422/34 |
| 3,650,038 | 3/1972 | Alessi et al. | 422/33 |
| 3,687,612 | 8/1972 | Ernst | 422/28 |
| 4,098,573 | 7/1978 | Gunther | 422/110 |
| 4,294,804 | 10/1981 | Baran | 422/112 |
| 4,301,113 | 11/1981 | Alguire et al. | 422/2 |
| 4,576,918 | 3/1986 | Yeung | 422/34 |
| 4,764,351 | 8/1988 | Hennebert et al. | 422/33 |
| 4,909,999 | 3/1990 | Cummings et al. | 422/292 |
| 5,209,902 | 5/1993 | Matthews et al. | 422/297 |
| 5,317,896 | 6/1994 | Sheth et al. | 73/29.01 |
| 5,364,590 | 11/1994 | Hillebrenner | 422/28 |
| 5,399,314 | 3/1995 | Samuel et al. | 422/34 |

OTHER PUBLICATIONS

"The 100% Solution: 3M's Steri–Vac™ System Eliminates CFCs Without Compromising Sterilization." 3M Health-Care Brochure, 1993.

"Steri–Vac™ 8XL Gas Sterilizer/Aerator Operator's Manual." 3M Health Care Operator's Manual, 23 pages, (1995).

Primary Examiner—Robert J. Warden
Assistant Examiner—E. Leigh Dawson
Attorney, Agent, or Firm—Gary L. Griswold; Walter N. Kirn; Jeffrey J. Hohenshell

[57] ABSTRACT

A sterilizer for sterilizing objects with biocidal gas which is designed to resist the deleterious effects of the biocidal gas. The invention provides a sterilizer having a sterilizing chamber for holding the objects to be sterilized, and a gas control system for manipulating the gaseous environment within the sterilizing chamber. The sterilizer has a vacuum control system, a vacuum line in fluid communication with the sterilizing chamber, a humidity sensor connected to that vacuum line at a point removed from or outside of the sterilizing chamber, and an isolation valve connected to the vacuum line at a point between the sterilizing chamber and the humidity sensor for temporarily isolating the humidity sensor from the sterilizing chamber. This arrangement assures that the humidity sensor received a sufficient sample for reading the adequacy of the humidification of the objects to be sterilized, while at the same time protecting it from the biocidal gas. In preferred embodiments, the sterilizer is provided with biocidal gas in disposable canisters intended to be positioned and locked inside the sterilizing chamber with the objects to be sterilized. At the appropriate time, the canister is punctured by a puncture apparatus. The preferred puncture apparatus has a metal bellows assembly that is particularly resistant to failure by chemical attack from the biocidal gas.

3 Claims, 2 Drawing Sheets

5,641,455

STERILIZER WITH GAS CONTROL

TECHNICAL FIELD

The present invention relates to a gas sterilizer, and more particularly to a sterilizer having improved control over the flow of biocidal gas.

BACKGROUND

A reliable supply of sterile instruments and supplies is vitally important to modem medical practice. Various types of apparatus are known for sterilizing reusable goods within a hospital setting including, for example, steam autoclaves. U.S. Pat. No. 4,301,113(Alguire et al); U.S. Pat. No. 4,294,804(Baran); U.S. Pat. No. 5,317,896(Sheth et al); U.S. Pat. No. 5,399,314(Samuel et al); U.S. Pat. No. 3,571,563 (Shulz); U.S. Pat. No. 3,054,270(Huston); and U.S. Pat. No. 3,564,861(Andersen et al), discuss sterilization apparatus and their control systems. Goods which cannot withstand autoclaving temperatures can be sterilized with sterilizers using a biocidal gas such as ethylene oxide.

Ethylene oxide sterilizers have a sterilizing chamber where the goods to be sterilized are placed. The door of the sterilizing chamber is then sealed, and the operator initiates a sterilizing cycle. For ethylene oxide to exert maximum effect, the goods should be pre-treated with the proper amount of humidity; to achieve this, a partial vacuum is drawn within the sterilizing chamber and then water is released into the chamber. When the correct amount of humidification has been achieved within the chamber, an appropriate charge of ethylene oxide gas is released and allowed to act on the surfaces of the goods for a period of time. Once the goods are sterile, the ethylene oxide gas is purged from the chamber and the chamber door is released so the goods can be unloaded.

The fact that ethylene oxide is toxic, flammable, and reactive over time with some plastic materials presents challenges to the design of these sterilizers. One challenge arises because the seals at the door of the sterilizing chamber are made of elastomeric plastic. It is very important to prevent the charge of ethylene oxide from being released if these seals are damaged: toxic gas must not be allowed into the room with the operator. A known method of insuring against this hazard is embodied in the Steri-vac™ Models 4XL and 5XL ethylene oxide sterilizers made by the Minnesota Mining and Manufacturing Company of St. Paul, Minn. In these sterilizers, the ethylene oxide gas is provided in a disposable canister which the operator places in a receptacle within the chamber after the goods have been loaded. The canister is punctured by a piston at the proper time during the sterilizing cycle. Because the piston can be moved only by vacuum within the chamber, and because the vacuum will never reach a sufficient level to move the piston if the chamber's seals are damaged, the gas will not be released if the seals are defective.

A challenge associated with this safety system is that the piston has a seal ring which is itself made of elastomeric plastic. Ethylene oxide may be absorbed into the piston seal and potentially cause it to fail, or the piston seal may react to impurities in the water or compressed air. When this occurs, the apparatus fails safely, i.e. the canister cannot be punctured and the biocidal gas remains contained, but the disruption in the expected flow of sterile instruments is a great inconvenience to the hospital staff.

A second challenge in sterilizer design is posed by the results of the effect of ethylene oxide gas on the humidity sensor. Such a sensor is present in conventional sterilizers in order to ensure that the goods have been pretreated to an appropriate level of humidity for the ethylene oxide to have its full effect. The reactive nature of the biocidal gas eventually damages the relatively delicate humidity sensor, causing it to fail. When this occurs, the apparatus once again fails safely, i.e. the damaged sensor indicates that the appropriate level of humidity has not been reached and the canister will not be punctured, but the failure again results in an inconvenient disruption of the orderly work of the hospital. From the foregoing, it is clear that the art requires designs for sterilizers which protect components which are sensitive to the side-effects of the biocidal gas.

SUMMARY OF THE INVENTION

The present invention alleviates the drawbacks of prior art by providing a biocidal gas sterilizer which reduces the deleterious effects of the biocidal gas on the gas release mechanism and the humidity sensor. The invention provides a sterilizer having a sterilizing chamber for receiving the objects to be sterilized, and a gas control system for manipulating the gaseous environment within the sterilizing chamber. The system for manipulating the gaseous environment has three major subsystems: a vacuum control system which can be connected to a vacuum source for evacuating the sterilizing chamber, a water vapor control system for injecting a selectable quantity of water into the sterilizing chamber, and a biocidal gas control system for controlling the release of biocidal gas. Importantly, the vacuum control system has a vacuum line in fluid communication with the sterilizing chamber. A humidity sensor for measuring the humidity of gas flowing from the sterilizing chamber connected to that vacuum line at a point removed from or outside of the sterilizing chamber. An isolation valve is connected to the vacuum line at a location between the sterilizing chamber and the humidity sensor. The isolation valve is adapted to temporarily isolate the humidity sensor from the sterilizing chamber. This arrangement assures that the humidity sensor gets a sufficient sample for reading the adequacy of the humidification of the objects to the sterilized, while at the same time protecting the humidity sensor from the biocidal gas. In preferred embodiments, the humidity sensor is connected to a branch vacuum line off the main vacuum line, and the isolation valve isolates the branch line when necessary to protect the humidity sensor.

Preferably, the sterilizer will be provided with biocidal gas in disposable canisters intended to be positioned and locked inside the sterilizing chamber with the objects to be sterilized. At the appropriate time, the canister is punctured by a puncture apparatus. A preferred puncture apparatus has a metal bellows assembly that is particularly resistant to failure by chemical attack from the biocidal gas.

The invention can also be viewed as a method of sterilizing objects with biocidal gas. The method comprises the steps of providing a sterilizing chamber for receiving the objects to be sterilized; providing a vacuum line having two branches in fluid communication with the sterilizing chamber, one of the branches having a humidity sensor and an isolation valve between the humidity sensor and the sterilizing chamber; drawing a partial vacuum within the humidity chamber via the vacuum line; injecting water vapor into the sterilizing chamber; evaluating the humidification within the sterilizing chamber by drawing a sample of gas from the sterilizing chamber through the vacuum line and into contact with the humidity sensor; closing the isolation valve when the humidity sensor detects that the humidification within the sterilizing chamber has reached a pre-selected level; and releasing biocidal gas within the sterilizing chamber. The releasing step is preferably performed with a puncture apparatus as described above.

BRIEF DESCRIPTION OF THE DRAWING

The present invention will be further described with reference to the accompanying drawing wherein like reference numerals refer to like parts in the several views, and wherein.

DETAILED DESCRIPTION

Figure 1:
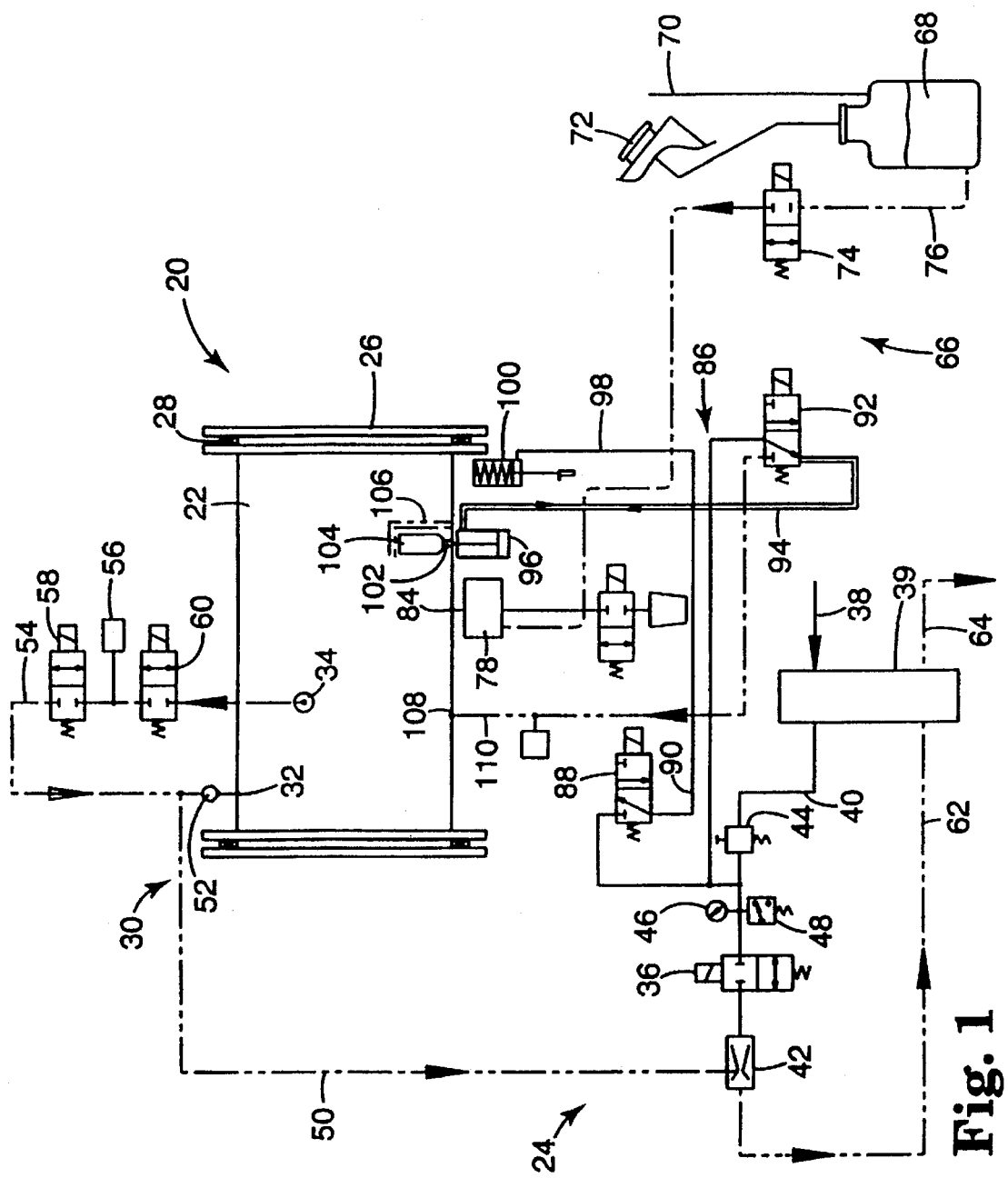
FIG. 1 is a schematic diagram of a sterilizer according to the present invention, detailing the flow of fluids through the apparatus.

Referring now to FIG. 1, a schematic diagram of a sterilizer 20 according to the present invention is illustrated. The sterilizer 20 includes a sterilizing chamber 22 for holding the objects to be sterilized. The sterilizing chamber 22 comprises the volume capable of receiving the goods to be sterilized.

The sterilizer 20 also includes a gas control system 24 for manipulating the gaseous environment within the sterilizing chamber 22. The sterilizing chamber 22 has a door 26 which can be opened to load or unload objects from the sterilizing chamber 22, or closed, in which case seal 28 provides a gas tight environment within the sterilizing chamber but for the ports of the gas control system 24 as discussed below.

In ethylene oxide sterilizing, it is necessary to subject the objects to be sterilized to a substantial vacuum as a pretreatment prior the introduction of the biocidal ethylene oxide gas in order to assure complete penetration of the gas. In the depicted embodiment this is accomplished by a vacuum control system 30. The vacuum control system 30 is in fluid communication with the sterilizing chamber 22 via ports 32 and 34. When it is desired to draw the initial vacuum in the sterilizing chamber 22, vacuum control valve 36 is activated, which allows pressurized air from air source 38 to flow through manifold 39 and tube 40 to venturi 42. Although a venturi system is depicted, the artisan will perceive that a vacuum pump could alternatively be used to supply the vacuum. The pressurized air in tube 40 is conditioned and measured by regulator 44, pressure gauge 46, and pressure switch 48. When venturi 42 is operated, a vacuum is drawn on line 50, and the gas in sterilizing chamber 22 is withdrawn via port 32 through check valve 52. A branch line 54 also connects to sterilizing chamber 22 through port 34.

The gas in branch line 54 is monitored by humidity sensor 56. A model 107–0205 humidity sensor, commercially available from Hy-Cal Engineering of El Monte, Calif., is considered particularly suitable. The flow of gas past humidity sensor 56 is conditional, based on the states of humidity sensor check valve 58 and humidity sensor isolation valve 60. The exhaust from the venturi 42 is carried away through line 62, through manifold 39 and though an outlet 64 to appropriate pollution abatement equipment.

In ethylene oxide sterilizing, it is also necessary to pretreat the objects with the proper amount of humidity prior to the introduction of the biocidal gas. To accomplish this function, the sterilizer 20 has a water vapor control system 66 for injecting a selectable quantity of water into sterilizing chamber 22. Distilled water for this purpose is stored in water container 68, the water container having an air vent tube 70 to allow the water in the water container to be displaced, and a fill port 72. After a vacuum has been drawn in the sterilizing chamber 22 and held for an appropriate time, it is then required to introduce the water, and water control valve 74 is opened. Water from water container 68 then flows through line 76 into heat sink 78 where it is heated. The water vapor then enters sterilizing chamber 22 via port 84.

As the water vapor enters the chamber and is allowed to contact the objects placed therein for sterilizing, humidity sensor check valve 58 and humidity sensor isolation valve 60 are opened, and a small amount of vacuum is drawn through branch line 54 past humidity sensor 56, which monitors the humidity history of the objects in the sterilizing chamber 22. When the objects are ready for the release of the biocidal gas, humidity sensor isolation valve 60 closes to protect the vulnerable humidity sensor 56 from contact with the biocidal gas.

When release of the biocidal gas is appropriate, a biocidal gas control system 86 ensures that this is done safely. During the vacuum and humidity conditioning periods, pressure from the regulator 44 has been passed from through door interlock valve 88 in its energized state through line 90 to puncture control valve 92, which is kept de-energized. Pressurized gas is passed through puncture control valve 92 via line 94 to puncture apparatus 96, and via line 98 to door interlock cylinder 100 to insure that the puncture apparatus is kept in the retracted position. Puncture apparatus 96 is positioned to be able to act through a sealed port 102 in sterilizing chamber 22 to puncture a disposable canister 104 of biocidal gas held within a specially shaped receptacle 106 within sterilizing chamber 22. When release of the biocidal gas is desired, valve 92 is energized, and partial vacuum from the sterilizing chamber 22 passed through port 108, into line 110, through puncture control valve 92, through line 94, and into puncture apparatus 96. As will be seen with more particularity below, puncture apparatus 96 can only be made to puncture canister 104 by vacuum, not by pressure. If, for example seal 28 was compromised so that release of the biocidal gas from canister 104 was a hazard to those outside the sterilizer 20, it would not be possible for the compromised vacuum in line 110 to activate puncture apparatus 96 to cause that release.

Figure 2:
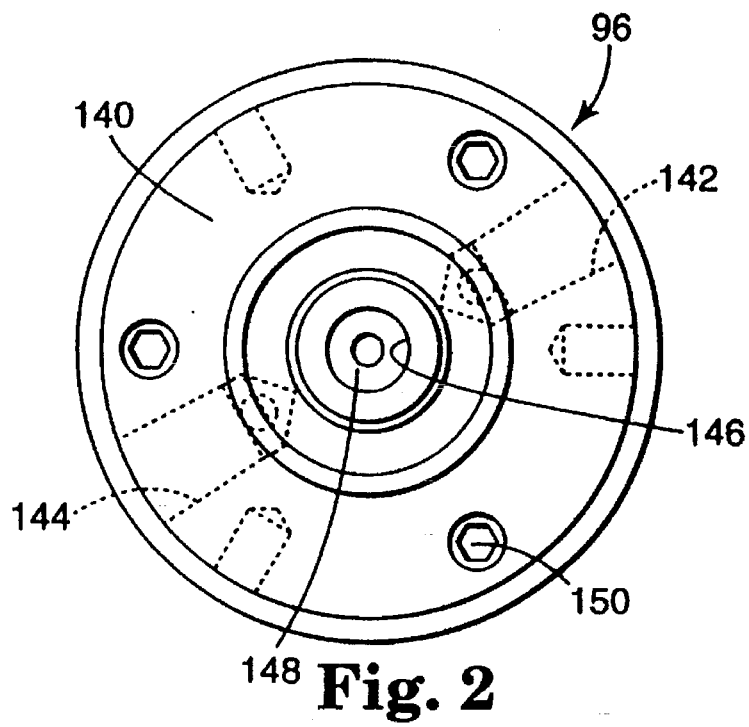
FIG. 2 is a top view of a puncture apparatus according to the invention.

Referring now to FIG. 2, a top view of a preferred puncture apparatus 96 according to the present invention is illustrated. An endcap 140 is provided, which is adapted to be fitted to port 102 in sterilization chamber 22. It is convenient to have two ports 142 and 144 in the endcap for delivering pressure or vacuum into the puncture apparatus 96, intending to cap one of them off during final assembly of the sterilizer 20. This ensures that the port used for connection is conveniently located for later servicing, no matter what orientation the puncture apparatus assumes when it is tightened into place in port 102. The ports 142 and 144 are conveniently tapered pipe threads. A moveable shaft 146 can be seen, having a threaded hole 148 in its end adapted for receiving a puncturing point having a complementary thread. Several bolts 150 are conveniently used to hold the assembled puncture apparatus together.

Figure 3:
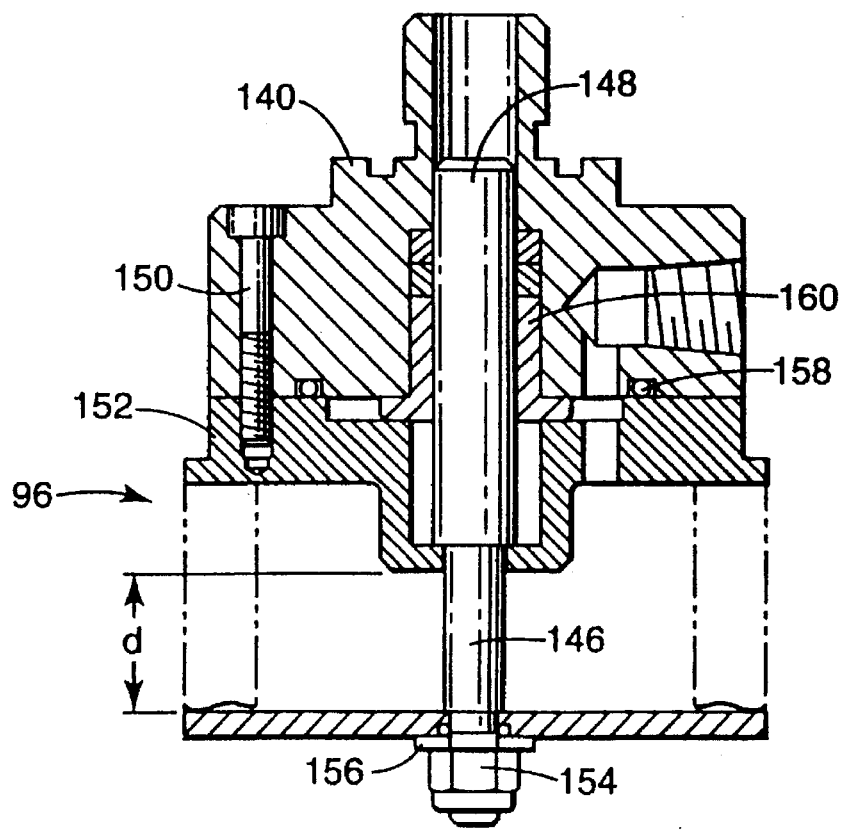
FIG. 3 is a side cross-section side view of the puncture cylinder of FIG. 2.

Referring now to FIG. 3, the puncture apparatus 96 is seen in side cross-section. Endcap 140 is attached to a corrosion resistant bellows assembly 152. A bellows assembly 152 which is considered particularly suitable has been constructed to adapt to the depicted end cap 140 by John Crane Belfab of Daytona Beach, Fla. The shaft 146 is conveniently attached to the bellows assembly 152 with a nut 154, sealed with an o-ring 156. An o-ring made of ethylene-propylenerubber (EPR) is considered preferred for this application. A similar o-ring 158 seals the junction between the endcap 140 and the bellows assembly 152. A bushing 160 is packed by a resistant seal; one commercially available as part number 305–205 from Bal-seal of Santa Ana, Calif. is considered particularly suitable.

The timing of the various actuation events described in connection with the above description is conveniently accomplished by microcontroller in ways which are well known to the ordinary artisan. A type 68HC11 microcontroller, commercially available from Motorola of Phoenix, Ariz., is considered particularly suitable.

The present invention has now been described with reference to several embodiments thereof. It will be apparent to those skilled in the art that many changes or additions can be made in the embodiments described without departing from the scope of the present invention. Thus, the scope of the present invention should not be limited to the structures described in this application, but only by structures described by the language of the claims and the equivalents of those structures.

What is claimed is:

1. A sterilizer for sterilizing objects with biocidal gas, comprising:

a sterilizing chamber for receiving objects to be sterilized, and a control system for manipulating the gaseous environment within the sterilizing chamber, the control system comprising:

a vacuum control system which can be connected to a vacuum source for evacuating the sterilizing chamber, a water control system which can be connected to a water source for injecting a selectable quantity of water into the sterilizing chamber, and a biocidal gas control system which can be connected to a biocidal gas source for controlling the release of biocidal gas, wherein the vacuum control system comprises:

a vacuum line in fluid communication with the sterilizing chamber, a humidity sensor connected to the vacuum line at a location removed from the sterilizing chamber for measuring the humidity of gas flowing from the sterilizing chamber through the vacuum line, and an isolation valve connected to the vacuum line at a location between the sterilizing chamber and the humidity sensor for temporarily isolating the humidity sensor from the sterilizing chamber.

2. A sterilizer for sterilizing objects with biocidal gas according to claim 1 wherein the vacuum line comprises a main vacuum line in fluid communication with the sterilizing chamber, and a branch vacuum line attached to the main vacuum line, and wherein the humidity sensor is connected to branch vacuum line so that the isolation valve can activate to isolate the branch line to isolate the humidity sensor from the sterilizing chamber.

3. A method of sterilizing objects with biocidal gas, comprising the steps of:

(1) providing a sterilizing chamber for receiving objects to be sterilized;

(2) providing a vacuum line having two branches in fluid communication with the sterilizing chamber, one of the branches having a humidity sensor and an isolation valve between the humidity sensor and the sterilizing chamber;

(3) inserting objects to be sterilized within the sterilizing chamber and sealing the sterilizing chamber;

(4) drawing a partial vacuum within the sterilizing chamber through the vacuum line;

(5) injecting water into the sterilizing chamber, (6) evaluating the humidification within the sterilizing chamber by drawing a sample of gas from the sterilizing chamber through the vacuum line and into contact with the humidity sensor;

(7) closing the isolation valve when the humidity sensor detects that the humidification within the sterilizing chamber has reached a pre-selected level; and (8) releasing biocidal gas within the sterilizing chamber causing the objects to be sterilized.

\* \* \* \* \*